United States Patent [19]

Takai et al.

[11] Patent Number: 4,859,673
[45] Date of Patent: Aug. 22, 1989

[54] AMIDE DERIVATIVES AND ANTIALLERGIC AGENTS CONTAINING THE SAME

[75] Inventors: Makoto Takai, Hochioji; Kazuhiro Omori; Takahiro Kumonaka, both of Kawasaki; Shinji Ozawa, Tokyo; Toshio Wakabayashi, Tama, all of Japan

[73] Assignee: Terumo Kabushiki Kaisha, Tokyo, Japan

[21] Appl. No.: 41,441

[22] Filed: Apr. 23, 1987

[30] Foreign Application Priority Data

Apr. 28, 1986 [JP] Japan ................................. 61-96638

[51] Int. Cl.$^4$ ................. C07D 405/00; C07D 211/22; C07D 211/56; C07D 413/00
[52] U.S. Cl. ..................... 514/255; 546/214; 546/221; 546/224; 544/367; 544/396; 514/326; 514/327; 514/329
[58] Field of Search ........... 546/214, 221, 224; 544/367, 396; 514/326, 327, 255, 329

[56] References Cited

U.S. PATENT DOCUMENTS 4,070,484 1/1978 Harita et al. .................. 546/214
4,673,684 6/1987 Wakabayashi et al. ........ 546/214

FOREIGN PATENT DOCUMENTS 0113226 7/1984 European Pat. Off. ............ 546/214
0157420 10/1985 European Pat. Off. ............ 546/214
0226516 6/1987 European Pat. Off. ............ 546/214
214766 10/1985 Japan .................................. 546/214
809760 3/1959 United Kingdom ................ 546/214

OTHER PUBLICATIONS

Chemical Abstracts, vol. 103, No. 8, Jul. 1985, Abstract No. 16527h, Columbus, Ohio, U.S.
Chemical Abstracts, vol. 104, No. 8, 1986, p. 500, Abstract No. 50683m, Columbus, Ohio, U.S.

*Primary Examiner*—Mary C. Lee
*Assistant Examiner*—Robert C. Whittenbaugh
*Attorney, Agent, or Firm*—Burns, Doane, Swecker & Mathis

[57] ABSTRACT

Novel amide derivatives are disclosed. As examples of said amide derivatives are mentioned 1-[2-(5-(3-methoxy-4-benzyloxyphenyl)-2,4-pentadienoyl)aminoethyl]-4-diphenylmethoxypiperidine, 1-[2-(5-(3-methoxy-4-pentadienoyl)aminoethyl]-4-diphenylmethoxypiperidine and 1-[2-(5-(3-methoxy-4-ethoxymethoxyphenyl)-2,4-pentadienoyl)aminoethyl]-4-diphenylmethoxypiperidine. These amide derivatives are useful as antiallergic agents.

5 Claims, No Drawings

AMIDE DERIVATIVES AND ANTIALLERGIC AGENTS CONTAINING THE SAME

BACKGROUND OF THE INVENTION (1) Field of the Invention

The present invention relates to novel amide derivatives and antiallergic agents containing the same. The amide derivatives provided by the invention inhibit the passive cutaneous anaphylaxis reaction (PCA reaction, Naohiko Watanabe, Akio Kobayashi; Int. Archs Allergy Appl. Immun. 72, pp 53–58, S. Karger AG, Basel, 1983) in rats which is associated with the onset of allergy. The amide derivatives of the invention, therefore, are useful as an antiallergic agent.

(2) Description of the Prior Arts

A variety of compounds are known as possessing antiallergic activities, but there are no surely effective therapeutic agents, and development of drugs with improved efficacy is desired.

SUMMARY OF THE INVENTION

As a result of extensive studies on the synthesis of a variety of amide derivatives and their PCA reaction-inhibitory activities in rats, we have found that the amide derivatives according to the present invention have potent inhibitory activities of the PCA reaction in rats. The invention has been completed on the basis of the above finding.

It is an object of the invention to provide novel amide derivatives and antiallergic agents containing the same.

According to the invention, there are provided amide derivatives represented by the general formula (I)

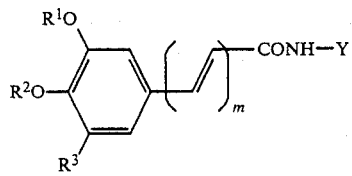

wherein $R^1$ and $R^2$ may be the same or different and each represents a lower alkyl group, a benzyl group, a tetrahydrofuranyl group, a lower alkoxy (lower)alkyl group or a lower alkoxycarbonyl group, $R^3$ represents a hydrogen atom or a lower alkoxy group, m represents an integer of 1 or 2 and Y represents a group of the formula (II), (III) or (IV),

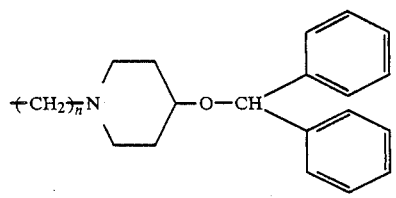

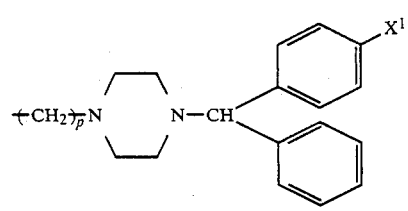

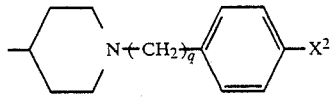

wherein $X^1$ and $X^2$ may be the same or different and each represents a hydrogen atom, a halogen atom or a lower alkoxy group, n, p and q each represents an integer of 1 to 4, provided that when $R^1$ and $R^2$ may be the same or different and each represents a lower alkyl group or a lower alkoxycaronyl group, Y does not represent a group of the above formula (II) or (III).

Further, according to the invention there are provided antiallergic agents containing an amide derivative represented by the above-mentioned formula (I).

Further, according to the invention there is provided a therapeutic method of allergic conditions which comprises administering animals with an effective dose of an amide derivative represented by the above-mentioned formula (I).

DETAILED DESCRIPTION OF THE INVENTION

In the above definition for the substituents $R^1$–$R^3$, $X^1$ and $X^2$ in the formula (I), the term "lower alkyl group" means a straight or branched chain alkyl group having from 1 to 4 carbon atoms, which is preferably methyl, ethyl, n-propyl or isopropyl, and the term "lower alkoxy group" means a straight or branched chain alkoxyl group having from 1 to 4 carbon atoms, which is preferably methoxy, ethyoxy, n-propoxy or isopropoxy. As the halogen atom is preferred fluorine, chlorine or bromine.

The amide derivatives represented by the abovementioned formula (I) are produced by reacting a reactive derivative of a carboxylic acid represented by the formula (V),

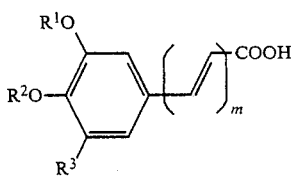

wherein $R^1$, $R^2$, $R^3$ and m have the same meanings as defined above with an amine derivative represented by the formula (VI)

$$H_2N-Y \qquad (VI)$$

wherein Y has the same meaning as defined above.

As the reactive derivative of the above-mentioned carboxylic acids (V) is preferably employed an acid halide, for example, the chloride or bromide, an anhydride or a mixed acid anhydride, for example, the mixed acid anhydride with ethylcarbonic acid.

The above-described reaction is carried out by a method known per se. For example, to a solution of a reactive derivative of the carboxylic acid (V) dissolved in an appropriate organic solvent such as, for example, dichloromethane or chloroform is added the amine derivative (VI), and the mixture is reacted at room temperature for several hours. The desired product (I) is isolated from the reaction mixture by conventional procedures and purified by such means as recrystallization or column chromatography.

The amide derivatives of the invention are used as an antiallergic agent. The dosage, which may be variable depending upon conditions of the disease, is generally 1-1000 mg and preferably 10-500 mg per day in adults, divided into one to three doses as required for the conditions. The administration may be in any suitable form, oral administration being particularly preferred but intravenous administration also being acceptable.

The compound of the invention may be administered as the active component or one of the active components either alone or in admixture with pharmaceutical carriers or excipients formulated by a conventional process into tablets, sugar-coated tablets, powders, capsules, granules, suspension, emulsion, injectable solution or the like. As examples of the carrier or excipient are mentioned calcium carbonate, calcium phosphate, starch, glucose, lactose, dextrin, alginic acid, mannitol, talc, and magnesium stearate.

Examples and a test example will be given below to describe in more details, but they are not intended to limit the invention in any way.

EXAMPLE 1

To a solution of 2.0 g (9.08 mmol) of 5-(3-methoxy-4-hydroxyphenyl)-2,4-pentadienoic acid in 90 ml of acetone was added 2.76 g (19.97 mmol) of anhydrous potassium carbonate and 2.30 ml (19.99 mmol) of benzyl chloride, successively, followed by heating under reflux for 15 hours. The mixture was concentrated under reduced pressure, diluted with water and extracted with chloroform. The organic layer obtained was dried over anhydrous sodium sulfate and concentrated under reduced pressure to give 4.01 g of a residue.

To a solution of the residue in 55 ml of a 10:1 mixture of methanol and water was added 1.82 g (45.5 mmol) of sodium hydroxide and the mixture was heated under reflux for 16 hours. The mixture was concentrated under reduced pressure, diluted with water and ice-cooled. The mixture was adjusted to pH 1 with a 6N hydrochloric acid aqueous solution and precipitated crystals were collected on a filter and dried in a vacuum desiccator to afford 2.62 g (8.44 mmol) of 5-[3-methoxy-4-(benzyloxy)phenyl]-2,4-pentadienoic acid.

To a solution of 3.50 g (7.94 mmol) of 1-β-(N-phthaloyl)aminoethyl-4-diphenylmethoxypiperidine in 70 ml of ethanol was added 0.52 g (8.31 mmol) of 80% hydrazine hydrate, followed by heating under reflux for 2 hours and concentrating under reduced pressure to give 4.10 g of a residue.

To a solution of the residue suspended in 90 ml of ethanol were added 2.46 g (7.93 mmol) of 5-(3-methoxy-4-benzyloxyphenyl)-2,4-pentadienoic acid, 1.80 g (8.72 mmol) of N,N'-dicyclohexylcarbodiimide and 0.10 g (0.82 mmol) of 4-dimethylaminopyridine, successively, followed by stirring at room temperature for 20 hours. The reaction mixture was filtered and the resulting organic layer was concentrated under reduced pressure. 5.5 g of the residue was subjected to silica gel column chromatography to give 2.53 g (4.20 mmol) of 1-[2-(5-(3-methoxy-4-benzyloxyphenyl)-2,4-pentadienoyl-)aminoethyl]-4-diphenylmethoxypiperidine from an eluate of chloroform-methanol (100:1). Spectrophotometric data of the product support the following structural formula (VII).

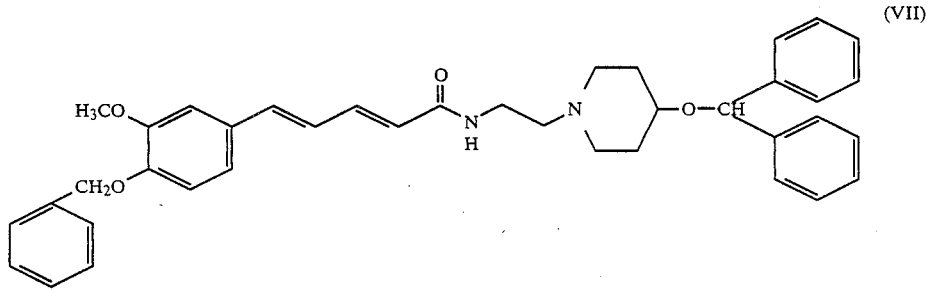

H - NMR(CDCl$_3$) δ: 6.4–7.6(21H, m), 6.10(1H, t, J=5 Hz), 5.89(1H, d, J=16 Hz), 5.49(1H, s), 5.12 (2H, s), 3.89(3H, s), 1.3–3.6(13H, m)

IR: ν (cm$^{-1}$ KBr): 3270, 1665, 1645, 1610, 1595, 1565, 1510

EXAMPLE 2

To a solution of 2.0 g (9.08 mmol) of 5-(3-methoxy-4-hydroxyphenyl)-2,4-pentadienoic acid in 90 ml of dry methylene chloride was added 1.51 ml (19.98 mmol) of 2.3-dihydrofuran and 229 mg (0.91 mmol) of pyridinium p-toluenesulphonic acid, successively, followed by stirring at room temperature for 16 hours. The mixture was washed successively with a saturated aqueous sodium hydroxide solution and water, and the resulting organic layer was dried over anhydrous sodium sulfate and concentrated under reduced pressure to give 4.07 g of a residue.

To a solution of the residue in 55 ml of a 10:1 mixture of tetrahydrofuran and water was added 1.63 g (40.8 mmol) of sodium hydroxide and the mixture was heated under reflux for 14 hours. The mixture was concentrated under reduced pressure, diluted with water and ice-cooled. The mixture was adjusted to pH 6.5 with a 1N hydrochloric acid aqueous solution and precipitated crystals were collected on a filter and dried in a vacuum desiccator to afford 2.56 g (8.82 mmol) of 5-[3-methoxy-4-(2-tetrahydrofuranyl)oxyphenyl]-2,4-pentadienoic acid.

To a solution of 4.55 g (10.33 mmol) of 1-β-(N-phthaloyl)aminoethyl-4-diphenylmethoxypiperidine in 75 ml of ethanol was added 0.71 g (11.36 mmol) of 80% hydrazine hydrate, followed by heating under reflux for 2 hours and concentrating under reduced pressure to give 5.26 g of a residue.

To a solution of the residue suspended in 100 ml of methylene chloride were added successively 2.50 g (8.61 mmol) of 5-(3-methoxy-4-(2-tetrahydrofuranyl)oxyphenyl)-2,4-pentadienoic acid, 1.95 g (9.47 mmol) of N,N'-dicyclohexylcarbodiimide and 0.11 g (0.90 mmol) of 4-dimethylaminopyridine, followed by stirring at room temperature for 19 hours. The reaction mixture was filtered and the resulting organic layer was concentrated under reduced pressure. 6.0 g of the residue was subjected to silica gel column chromatography to give 2.68 g (4.60 mmol) of 1-[2-(5-(3-methoxy-4-(2-tetrahydrofuranyl)oxyphenyl)-2,4-pentadienoyl)aminoethyl]-4-diphenylmethoxypiperidine from an eluate of chloroform-methanol (100:1). Spectrophotometric data of the product support the following structural formula (VIII).

methoxy-4-benzyloxyphenyl)-2,4-pentadienoic acid in Example 1 to obtain 5.53 g (9.7 mmol) of 1-[2-(5-(3-methoxy-4-ethoxymethoxyphenyl)-2,4-pentadienoyl)aminoethyl]-4-diphenylmethoxypiperidine. The spectrophotometric data of the product support the following structural formula (IX).

H - NMR(CDCl₃) δ (ppm): 1.20(3H, t, J=7.5 Hz). 3.73(2H, q, J=7.5 Hz), 3.85(3H, s), 5.23(2H, s), 5.47(1H,

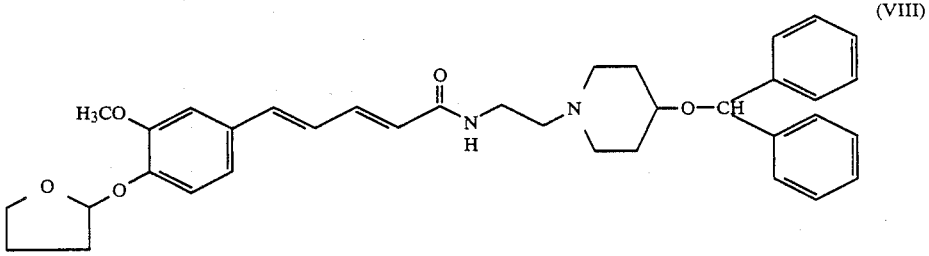

(VIII)

H - NMR(CDCl₃) δ: 6.4–7.6(16H,m), 6.17(1H, t, J=5 Hz), 5.89(1H, d, J=16 Hz), 5.76(1H, bs), 5.43(1H, s), 3.77(3H, s), 3.1–4.3(5H, m), 1.2–3.0(14H, m)
IR: ν (cm⁻¹ CHCl₃): 3400, 1660, 1620, 1600, 1510 s), 5.92(1H, d, J=14 Hz)
IN: ν (cm⁻¹, CHCl₃) 3400, 1660, 1620, 1600

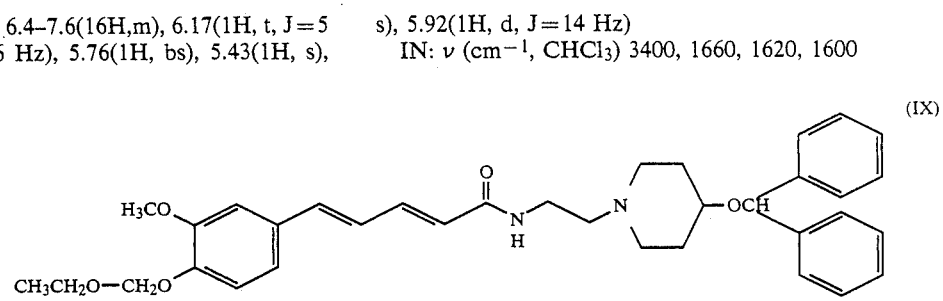

(IX)

EXAMPLE 3

In 100 ml of dry ethylene chloride were dissolved 5.00 g (22.7 mmol) of 5-(3-methoxy-4-hydroxyphenyl)-2,4-pentadienoic acid and 11.87 ml of diisopropylethylamine in an argon atmosphere. To the solution was added dropwise 6.25 ml of chloromethyl ethyl ether at room temperature over 15 minutes. The mixture was left to stand at room temperature overnight, diluted with water and extracted three times with methylene chloride. The organic extract layer was washed with water and dried over anhydrous sodium sulfate. The solvent was distilled off under reduced pressure to give 8.66 g of a residue. The residue was subjected to silica gel column chromatography to afford 6.89 g (20.5 mmol) of ethoxymethyl 5-(3-methoxy-4-ethoxymethoxyphenyl)-2,4-pentadienoate from a fraction with chloroform.

6.00 g (17.8 mmol) of the ester was dissolved in 120 ml of methanol. To the resulting solution was added 30 ml of an aqueous solution containing 3.60 g of sodium hydroxide at room temperature. The mixture was left to stand at room temperature overnight. Methanol was distilled off from the reaction mixture under reduced pressure and the residue was made acidic with hydrochloric acid under ice cooling. The mixture was extracted three times with chloroform. The extract organic layer was washed with water and subsequently dried over anhydrous sodium sulfate. The solvent was distilled off from the extract under reduced pressure to afford 4.320 g (15.5 mmol) of 5-(3-methoxy-4-ethoxymethoxyphenyl)-2,4-pentadienoic acid.

4.260 g (15.3 mmol) of the carboxylic acid was subjected to a reaction similar to the reaction of 5-(3-

TEST EXAMPLE

DNP-ascaris (1 mg) prepared by combining a swine ascaris extract with 2,4-dinitrophenyl sulfate was mixe with 20 mg of aluminum hydroxide gel. The mixture was administered to rats subcutaneously on the back, and at the same time the animals were intraperitoneally given 2×10¹⁰ dead *Bordetella pertussis* respectively. The same procedures were repeated after 14 days, and blood sample was obtained after 21 days to produce antisera.

Female Sprague-Dawley strain rats (8 weeks old) were sensitized by subcutaneously administering 0.1 ml of 1:256 diluted antisera (titer=1024) respectively on the grained back. After 48 hours, groups of four rats were orally given the amide derivatives produced in the examples above at various concentrations. After one hour, the rats were challenged by intravenously administering a 0.5% physiological saline solution of Evans Blue containing 1 mg of the NDP-ascaris from the tail. After 30 minutes, the animal was sacrificed by bleeding and the portion of the skin with the dye exuded was cut off. The cut skin was treated with 1N-KOH solution, and the dye was extracted by adding 9 ml of 0.6N-phosphoric acid-acetone (5:13) mixture. The supernatant from centrifugal separation was measured for absorbancy at 620 nm to determine amount of the dye. Percent inhibition at each of the concentrations of the amide derivatives was calculated in comparison with amount of the dye for control group. Results are shown in Table-I. Percent inhibition of tranilast, an antiallergic agent commercially available from Kissei Pharmaceutical Co., Ltd. under the trade name of Rizaben against PCA reaction was also shown in Table-I. As shown in Table-I, the amide derivatives of the invention produced high PCA reaction-inhibitory effects.

Table I

| PCA reaction-inhibitory effects in rats | | |
|---|---|---|
| Test compound Example No. | Concentration (mg/kg) | Inhibition (%) mean ± SE |
| 1 | 30 | 0 ± 20 |
|   | 100 | 50 ± 14 |
| 2 | 10 | 51 ± 18 |
|   | 30 | 71 ± 6 |
| 3 | 30 | 55 ± 9 |
|   | 100 | 78 ± 8 |
| Control | 100 | 37 ± 8 |
| (Tranilast) | 200 | 40 ± 10 |
|   | 300 | 42 ± 5 |

It has been confirmed that amide derivatives of the invention not shown in Table-I also possess PCA reaction-inhibitory effects in rats. Acute Toxicity An acute toxicity test was conducted using male ICR mice (5 weeks old) by oral administration. $LD_{50}$ was 1000 mg/kg or higher with every compound of the invention to demonstrate high safety margin as compared with the effective dose.

What is claimed is:

1. A compound of the formula (I)

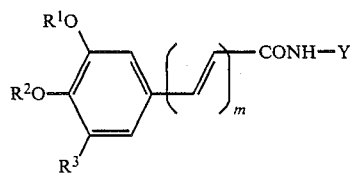

wherein $R^1$ and $R^2$ may be the same or different and each represents a lower alkyl group, a benzyl group, a tetrahydrofuranyl group, a lower alkoxy (lower)alkyl group or a lower alkoxycarbonyl group, $R^3$ represents a hydrogen atom or a lower alkoxy group, m represents an integer of 1 or 2 and Y represents a group of the formula (II), (III), or (IV).

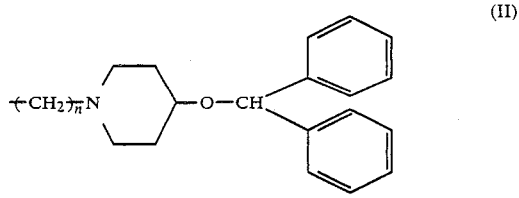

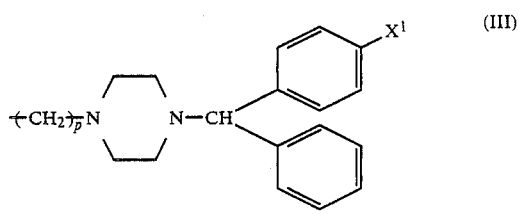

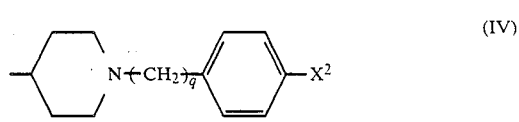

wherein $X^1$ and $X^2$ may be the same or different and each represents a hydrogen atom a halogen atom or a lower alkoxy group, n, p and q each represents an integer of 1 to 4, provided that when $R^1$ and $R^2$ may be the same or different and each represents a lower alkyl group or a lower alkoxycarbonyl/group, Y does not represent a group of the above formula (II) or (III).

2. The compound according to claim 1 wherein $R^1$ represents a lower alkyl group, $R^2$ represents a benzyl group, a tetrahydrofuranyl group, a lower alkoxy (lower) alkyl group, $R^3$ represents a hydrogen atom and Y represents a group of the above formula (IV).

3. The compound according to claim 1 which is 1-[2-(5-(3-methoxy-4-benzyloxyphenyl)-2,4-pentadienoyl-)aminoethyl]-4-diphenylmethoxypiperidine, 1-[2-(5-(3-methoxy-4-(2-tetrahydrophenyl)oxyphenyl)-2,4-pentadienoyl)aminoethyl]-4-diphenylmethoxypiperidine or 1-2-(5-(3-methoxy-4-ethoxymethoxyphenyl)-2,4-pentadienoyl)aminoethyl]-4-diphenylmethoxypiperidine.

4. A pharmaceutical composition for the treatment of allergic conditions having a passive cutaneous anaphylaxis reaction, said composition comprising an antiallergic effective amount of the compound of claim 1 and a pharmaceutically acceptable carrier therefor.

5. A method for the therapy of allergic conditions having a passive cutaneous anaphylaxis reaction which comprises administering to animals an antiallergic effective dose of the compound of claim 1.

* * * * *